US00PP33626P2

(12) United States Plant Patent
Read et al.

(10) Patent No.: US PP33,626 P2
(45) Date of Patent: Nov. 9, 2021

(54) ***LEUCANTHEMUM* PLANT NAMED 'REAL COMET'**

(50) Latin Name: ***Leucanthemum* x *superbum***
Varietal Denomination: Real Comet

(71) Applicants: Charles Richard Read, Bognor Regis (GB); Keith George Lintott, Bognor Regis (GB)

(72) Inventors: Charles Richard Read, Bognor Regis (GB); Keith George Lintott, Bognor Regis (GB)

( * ) Notice: Subject to any disclaimer, the term of this patent is extended or adjusted under 35 U.S.C. 154(b) by 0 days.

(21) Appl. No.: 17/174,079

(22) Filed: Feb. 11, 2021

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./263.1, 285
See application file for complete search history.

*Primary Examiner* — Susan McCormick Ewoldt
*Assistant Examiner* — Karen M Redden
(74) *Attorney, Agent, or Firm* — Weatherly IP Solutions LLC; James M. Weatherly

(57) ABSTRACT

A new cultivar of *Leucanthemum* plant named 'Real Comet' that is distinguishable by tight clumping basal branching and upright plant habit, double inflorescences consisting of inner whorls of golden-yellow ray florets and outer whorls of cream or pale yellow ray florets which are presented horizontally and downwards. Flowering of 'Real Comet' commences in late June and continues until October on plants which are 40 cm in height and 35 cm in width after 1 year of growth from an initial cutting.

2 Drawing Sheets

Figure 1:
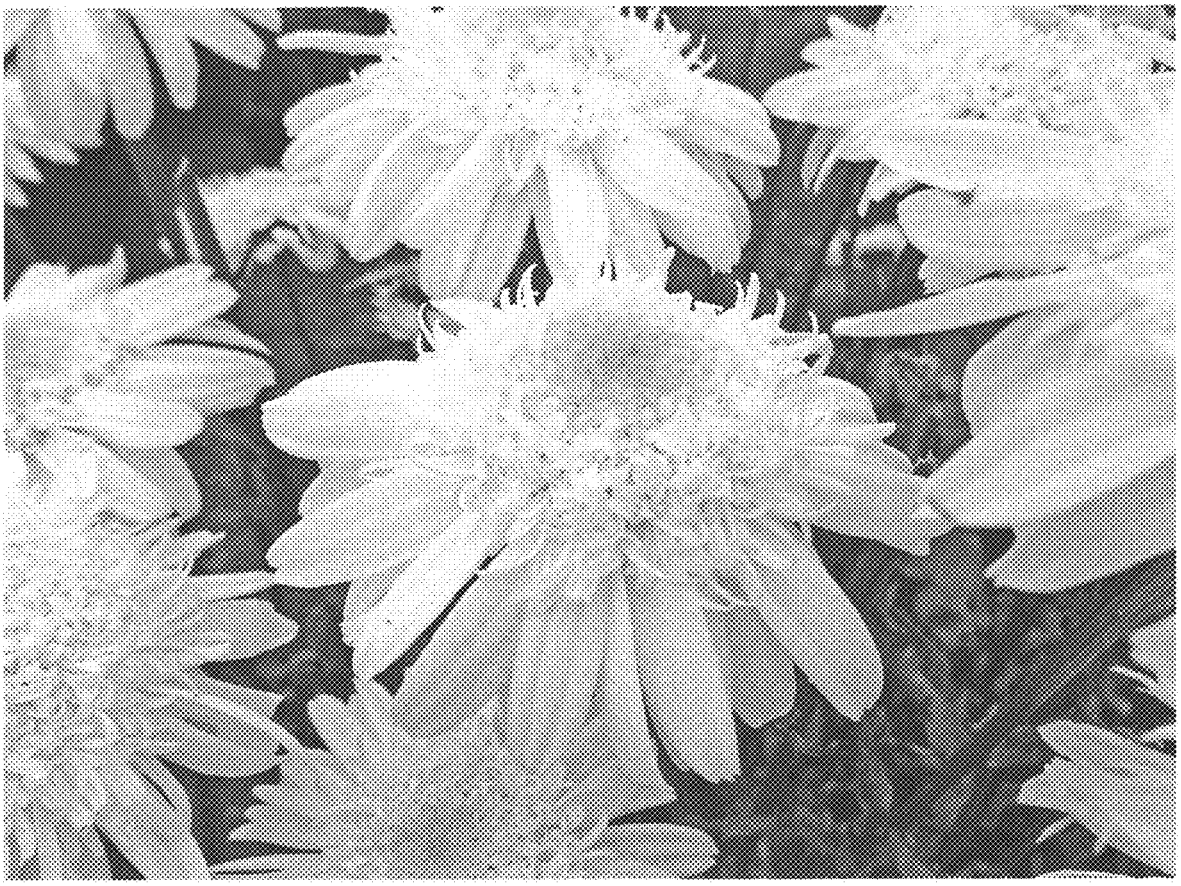

Genus and species: *Leucanthemum* x *superbum*.
Variety denomination: 'Real Comet'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Comet'. *Leucanthemum* is a genus within the family Asteraceae in which the commonly referred to "flower" is botanically the inflorescence which is comprised of outer showy ray florets surrounding smaller disc florets.

'Real Comet' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Comet' is a seedling selection that resulted from the controlled pollination in 2009 of a single plant of the inventors' proprietary *Leucanthemum* seedling code L830-5 (unreleased and unpatented) as the female parent, using pollen from a single plant of the inventors' proprietary *Leucanthemum* seedling code L800-3 (unreleased and unpatented) as the male parent. The inventors selected 'Real Comet' in 2012 for its combination of tight clumping basal branching and upright habit, numerous smaller-size cushion-centered flowers with pure white ray flowers which reflex as the flower expands.

'Real Comet' was first asexually propagated by the inventors in West Sussex, United Kingdom in 2012 using the method of vegetative division and subsequently by basal shoot cuttings. Since that time under careful observation 'Real Comet' has been determined uniform, stable and true to type in subsequent generations of asexual propagation.

SUMMARY

The following traits have been repeatedly observed and represent the distinguishing characteristics of 'Real Comet'. In combination these traits set 'Real Comet' apart from all other existing varieties of *Leucanthemum* known to the inventor. 'Real Comet' has not been tested under all possible conditions and phenotypic differences may be observed with variations in environmental, climatic, and cultural conditions, however, without any variance in genotype.

1. 'Real Comet' exhibits tight clumping basal-branching and an upright plant habit.
2. The foliage of 'Real Comet' is long and narrow.
3. A fully expanded inflorescence of 'Real Comet' is 7.5 cm. in diameter and is comprised of ray florets arranged around a central disc.
4. The ray florets of 'Real Comet' are arranged in 2 to 3 concentric whorls.
5. The ray florets of 'Real Comet' are white in color and presented horizontally until fully expanded, and gently reflexing thereafter.
6. The central disc of the inflorescence of 'Real Comet' appears as a cushion comprised of mid-yellow colored disc florets surrounded by rudimentary white ray florets which are short and curled.

7. The inflorescences of 'Real Comet' are carried on strong, stiff stems.
8. Flowering of 'Real Comet' commences in late June and continues until October.
9. After one year of growth in a 2 gallon container, or planted in the ground, a plant of 'Real Comet' is 40 cm in height and 35 cm in width.
10. 'Real Comet' is hardy in USDA Zone 5 (−20° F. or −28° C.).

COMPARISON WITH PARENTAL LINES AND KNOWN VARIETY

In comparison with the female parent, seedling code L830-5, 'Real Comet' exhibits a more-pronounced cushion-shaped center and white ray flowers. The ray flowers of L830-5 are off-white to cream in color. In comparison with the male parent, seedling code L800-3, 'Real Comet' bears single white ray flowers whereas the white ray flowers of L800-3 are both single and tubular. In addition, compared with both parents, the whole plant of 'Real Comet' is shorter and bears shorter flower stems.

The commercial variety of *Leucanthemum* which the inventors consider to most closely resemble 'Real Comet' is the inventors' variety of *Leucanthemum* Plant Named 'Real Glory' (U.S. Plant Pat. No. 25,733). In comparison with 'Real Glory', plants of 'Real Comet" are approximately 40% shorter in height, and bear flowers with a 10% lesser diameter.

BRIEF DESCRIPTION OF THE PHOTOGRAPHS

The accompanying color photographs were taken in July 2018 in Oxnard, Calif. The photographs illustrate the overall appearance of 'Real Comet' showing the color of foliage and inflorescence as true as is reasonably possible to obtain in color reproductions of this type. The illustrated plants have been grown out of doors, without any pruning or use of chemical growth regulators. The colors in the photographs may differ from color values cited in the detailed botanical description, which accurately describe the actual color of 'Real Comet'.

FIG. 1 presents a close-up view of the inflorescences of 'Real Comet'.

Figure 2:
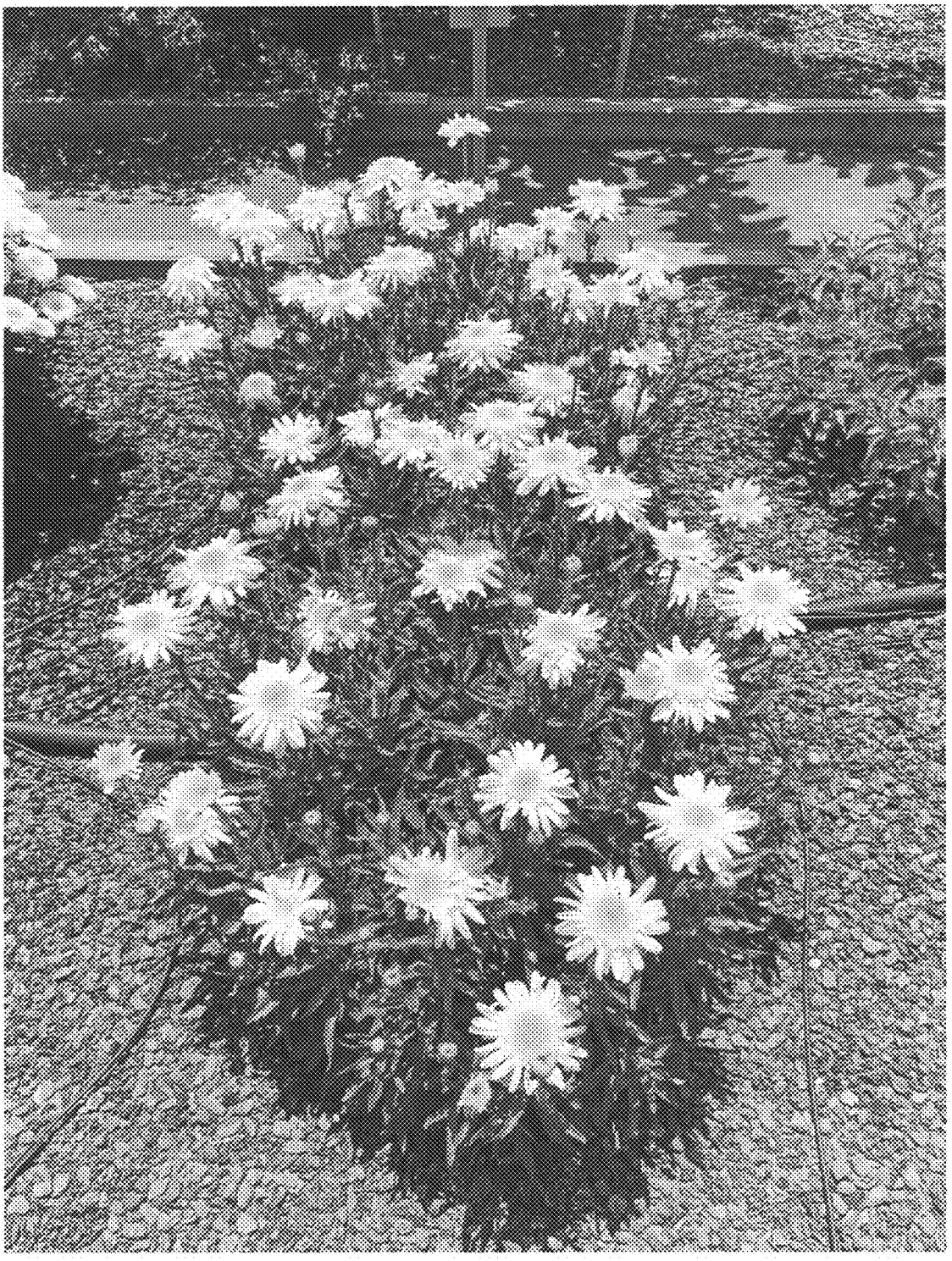

FIG. 2 illustrates two eighteen-months-old plants of 'Real Comet' which have been planted when six months old and grown outdoors for one season in Oxnard, Calif.

BOTANICAL DESCRIPTION OF THE PLANT

The following is a detailed botanical description of the new cultivar 'Real Comet'. Observations, measurements, values and comparisons were collected in Santa Barbara, Calif. during late June 2019, from a 1 year old plant growing outdoors in 2-gallon container. Color determinations are made in accordance with The 2007 Royal Horticultural Society Colour Chart from London, England, except where general color terms of ordinary dictionary significance are used.

Botanical classification:

*Family.*—Asteraceae (formerly Compositae).
*Genus.*—*Leucanthemum.*
*Species.*—x *superbum.*
*Denomination.*—'Real Comet'.
*Common name.*—Shasta daisy.
*Habit.*—Basal-branching upright growth habit.
*Commercial category.*—Perennial.
*Use.*—For garden and landscape.
*Suggested commercial container size.*—1 gallon, 2-gallon containers.
*Parentage.*—*Leucanthemum* x *superbum* 'Real Comet' is a seedling selection resulting from the controlled cross-pollination of the following parents: Female parent: *Leucanthemum* seedling code L830-5. Male parent: *Leucanthemum* seedling code L800-3.
*Propagation method.*—Basal shoot cuttings and division.
*Rooting system.*—Fine and fibrous.
*Vigor.*—Moderate with prolific basal branching.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—7 to 8 months to produce a flowering plant in a 1-gallon container starting from a rooted cutting. 10 months to produce a full plant in a 2-gallon container.
*Plant dimensions* (*one year*).—Height 40 cm. including the flowers which are held 20 cm above the foliage canopy; diameter 35 cm.
*Cultural requirements.*—Grow in full sun and rich, moist moderately fertile well-draining soil.
*Pest or disease resistance and susceptibility.*—No specific disease or pest resistance or susceptibility has been observed.
*Hardiness.*—USDA Zone 5.

Stem:

*Branching.*—Basal.
*Color.*—187A.
*Dimensions.*—Length, 15.0 cm; diameter at base 0.8 cm.
*Shape.*—Cylindrical.
*Surface.*—Smooth, glabrous.

Foliage:

*Type* (*division*).—Simple.
*Arrangement.*—Opposite.
*Internode distance* (*range*).—2.5 cm to 3.0 cm.
*Margin.*—Mostly regularly dentate; teeth 3 to 5 mm in length, angled towards leaf apex, spaced at approximately 8 mm intervals.
*Apex.*—Acute.
*Base.*—Attenuate.
*Leaf attachment.*—Sessile.
*Leaf color* (*adaxial surface*).—137A.
*Leaf color* (*abaxial surface*).—138A.
*Leaf shape.*—Lanceolate.
*Leaf dimensions* (*lower, oldest, leaves*).—19 cm in length, 2.5 cm in width.
*Leaf dimensions* (*upper, newest, leaves*).—5 cm to 7 cm in length, 1.5 cm in width.
*Leaf venation.*—Pinnate, but very faint.
*Vein color* (*both surfaces*).—As leaf, 137A (adaxial), 138A (abaxial) surfaces.
*Leaf surface* (*adaxial surface*).—Coriaceous, glabrous.
*Leaf surface* (*abaxial surface*).—Smooth, glabrous.

Inflorescence:

*Inflorescence type.*—Capitulum, consisting of ray florets and disc florets and a whorled array of rudimentary ray florets which emerge from the perimeter of the disc.

*Inflorescence quantity* (*average*).—30 (including colored buds).
*Inflorescence diameter* (*fully opened*).—7.5 cm.
*Inflorescence depth.*—4.5 cm.
*Inflorescence aspect.*—Upright.
*Inflorescence colors* (*when fully developed*).—Ray florets: NN155A. Disc: Inner (nearest to disc) ray florets: 12A. Central disc: 6B to 6C.
*Fragrance.*—Characteristic of freshly cut grass.
*Blooming season.*—Late June to October.
*Lastingness of inflorescence* (*range*).—10 to 14 days on the plant, 6 to 8 days as a cut flower.

Bud:
*Bud dimensions.*—0.8 cm in height and 1.2 cm in diameter.
*Bud shape.*—Flattened sphere.
*Bud color.*—138A, apex (cluster of involucral bracts) 183A.
*Bud surface.*—Glabrous.

Peduncle:
*Peduncle shape.*—Cylindrical.
*Peduncle length.*—13 cm to 24 cm.
*Peduncle diameter.*—3 mm to 4 mm.
*Peduncle surface.*—Furrowed, minutely pubescent, hair color silver-grey.
*Peduncle strength.*—Very strong and stiff.
*Peduncle color.*—138A.

Peduncle bracts:
*Arrangement.*—Single, alternate, rotate around peduncle.
*Quantity.*—2 to 4, spaced irregularly between 1 cm. and 6 cm. apart.
*Attachment.*—Sessile.
*Shape.*—Lanceolate, spiral.
*Margin.*—Minutely dentate.
*Apex.*—Acute.
*Base.*—Attenuate.
*Color* (*adaxial surface*).—137A.
*Color* (*abaxial surface*).—137D.
*Dimensions.*—2.5 cm to 3.0 cm in length, 3 mm. in width.
*Surface* (*adaxial surface*).—Coriaceous.
*Surface* (*abaxial surface*).—Smooth, glaucous.

Ray flowers:
*Ray flower arrangement.*—Single whorl with ray flowers densely and tightly packed.
*Shape.*—Strap-like, longitudinally furrowed.
*Quantity.*—35 to 40 ray flowers per inflorescence.
*Aspect.*—Borne horizontally until fully expanded, then slightly reflexed.
*Corolla tube dimensions.*—3 mm in length, 1 mm in diameter.
*Corolla tube color.*—144C.
*Ray flower petals.*—Shape: Strap-like, longitudinally furrowed. Surface (both surfaces): Glabrous. Apex: Emarginate (3 lobed). Margin: Entire. Dimensions: 30 mm in length, 9 mm. in width. Color (both surfaces): NN155D.

Involucral bracts:
*Quantity* (*average*).—45 to 50 per inflorescence, arranged in two overlapping whorls, fused at base.
*Bract color* (*abaxial and adaxial surfaces*).—137D.
*Bract length.*—9 to 10 mm.
*Bract width.*—3 mm.
*Bract apex.*—Rounded with tiny cilia.
*Bract base.*—Truncate.
*Bract surface* (*both surfaces*).—Glabrous.
*Bract shape.*—Lanceolate.
*Bract margin.*—Entire, smooth, color 183A.

Disc floret:
*Disc diameter.*—2.2 to 2.5 cm.
*Disc floret quantity* (*average*).—Approximately 200 to 225 per inflorescence.
*Disc color.*—17B to 17C.
*Disc floret dimensions.*—7 mm in length, 1 mm in diameter.
*Disc floret shape.*—Tubular.
*Disc floret petal quantity.*—Ranges from 3 to 5 in number, basally fused.
*Disc floret petal dimensions.*—3 mm in length, 0.75 mm in width.
*Disc floret petal color.*—17B to 17C.
*Disc floret petal apex.*—Acute.
*Disc floret petal base.*—Truncate.
*Disc floret corolla tube.*—3 mm in length, 0.5 mm in diameter, color 151D.

Reproductive organs:
*Ray flowers.*—Androecium (stamens, anthers, filaments, pollen): Absent. Pistil: 1, 3 mm in length, hair-like, diameter less than 0.2 mm., color light brown. Stigma: 2 mm in length, hair-like, diameter less than 0.2 mm, color light brown. Ovary (observed immature only): Superior, globose, less than 1 mm in diameter, color 145C.
*Disc flowers.*—Stigma, style, and ovary not observed. Stamens: 5, fused appearing as one, length 1 mm, color 175A. Pollen: None observed. Pistil: 1, less than 1 mm in length, stigma, style, ovary not observed.

Seed: None observed to date.

We claim:

1. A new and distinct cultivar of *Leucanthemum* plant named 'Real Comet' as described and illustrated herein.

* * * * *